(12) United States Patent
Crescenzi et al.

(10) Patent No.: US 12,239,990 B2
(45) Date of Patent: Mar. 4, 2025

(54) DEVICE AND METHOD FOR COLLECTING, PRESERVING AND/OR TRANSPORTING BIOLOGICAL SAMPLES

(71) Applicant: DIAPATH S.P.A., Martinengo (IT)

(72) Inventors: Anna Crescenzi, Rome (IT); Roberto Virgili, Rome (IT); Alberto Battistel, Martinengo (IT); Carmelo Lupo, Martinengo (IT); Paolo Danzi, Martinengo (IT); Giorgio Manenti, Martinengo (IT); Ottaviano Bussi, Martinengo (IT)

(73) Assignee: DIAPATH S.P.A., Martinengo BG (IT)

( * ) Notice: Subject to any disclaimer, the term of this patent is extended or adjusted under 35 U.S.C. 154(b) by 164 days.

(21) Appl. No.: 16/611,589

(22) PCT Filed: Oct. 10, 2017

(86) PCT No.: PCT/IB2017/056243
§ 371 (c)(1),
(2) Date: Nov. 7, 2019

(87) PCT Pub. No.: WO2018/207010
PCT Pub. Date: Nov. 15, 2018

(65) Prior Publication Data
US 2020/0156076 A1      May 21, 2020

(30) Foreign Application Priority Data

May 11, 2017 (IT) .......................... 102017000051294

(51) Int. Cl.
*B01L 3/00* (2006.01)
*A61B 10/00* (2006.01)

(52) U.S. Cl.
CPC ........ *B01L 3/5635* (2013.01); *A61B 10/0096* (2013.01); *B01L 2200/026* (2013.01);
(Continued)

(58) Field of Classification Search
CPC ............. B01L 3/5635; B01L 2200/026; B01L 2300/042; B01L 2300/044;
(Continued)

(56) References Cited

U.S. PATENT DOCUMENTS 4,592,934 A * 6/1986 Wolstoncroft ........... C09G 1/12
106/10
2009/0155838 A1* 6/2009 Hale ..................... A61J 1/2093
435/29
(Continued)

FOREIGN PATENT DOCUMENTS

| EP | 3 162 727 | 5/2017 | |
|---|---|---|---|
| WO | 2017016676 | 2/2017 | |
| WO | WO-2017016676 A1 * | 2/2017 | ......... A61B 10/0096 |

OTHER PUBLICATIONS

SK-Electronics Co., Ltd., What is IC Tag, 2014-2024 (Year: 2014).*
(Continued)

*Primary Examiner* — Matthew D Krcha
*Assistant Examiner* — Tingchen Shi

(57) ABSTRACT

The present invention relates to a device and method for collecting, preserving and/or transporting biological samples.

8 Claims, 11 Drawing Sheets

(52) U.S. Cl.
CPC ... *B01L 2300/042* (2013.01); *B01L 2300/044* (2013.01); *B01L 2300/049* (2013.01); *B01L 2300/0672* (2013.01); *B01L 2400/0683* (2013.01)

(58) Field of Classification Search
CPC ....... B01L 2300/049; B01L 2300/0672; B01L 2400/0683; A61B 10/0096
See application file for complete search history.

(56) References Cited

U.S. PATENT DOCUMENTS

| | | | |
|---|---|---|---|
| 2010/0323437 A1* | 12/2010 | Nakae | A61B 5/150351 435/307.1 |
| 2015/0037830 A1* | 2/2015 | Jakobsen | G01N 1/28 435/307.1 |
| 2017/0001191 A1 | 1/2017 | Biadillah et al. | |
| 2017/0016807 A1 | 1/2017 | Biadillah et al. | |

OTHER PUBLICATIONS

International search report and written opinion issued on Dec. 6, 2017 for PCT/IB2017/056243.

* cited by examiner

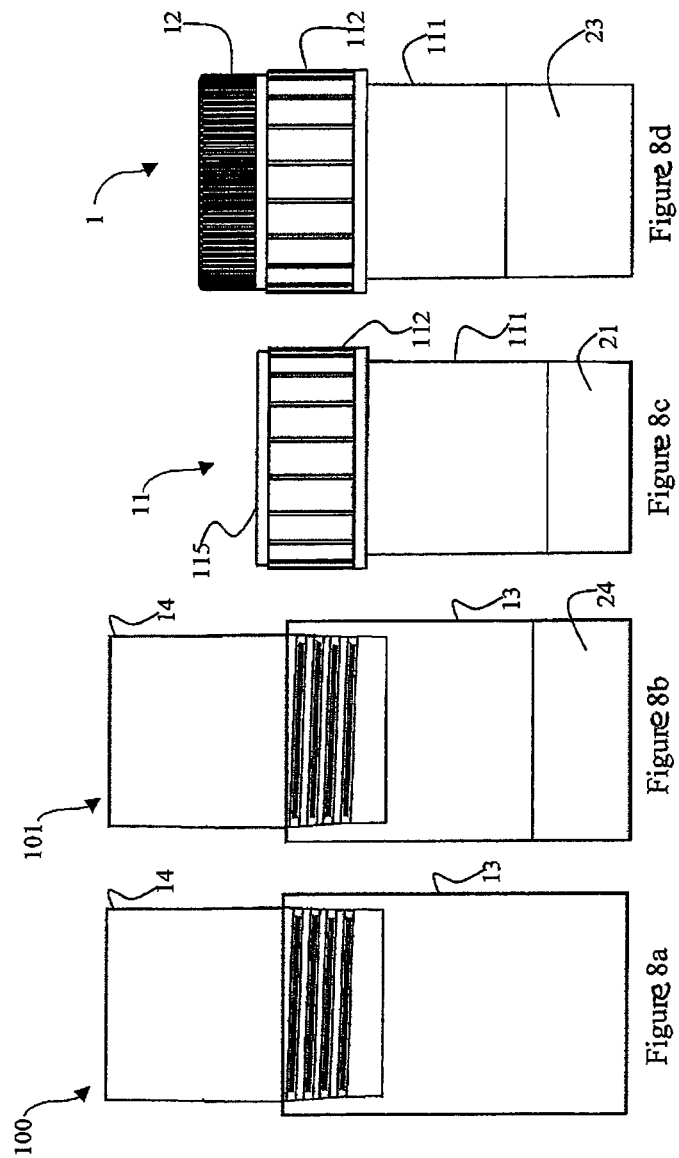

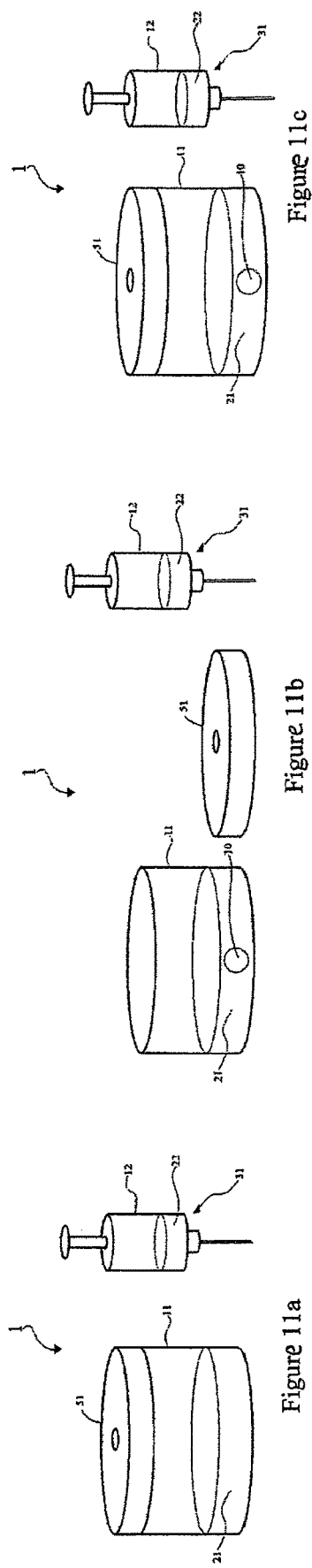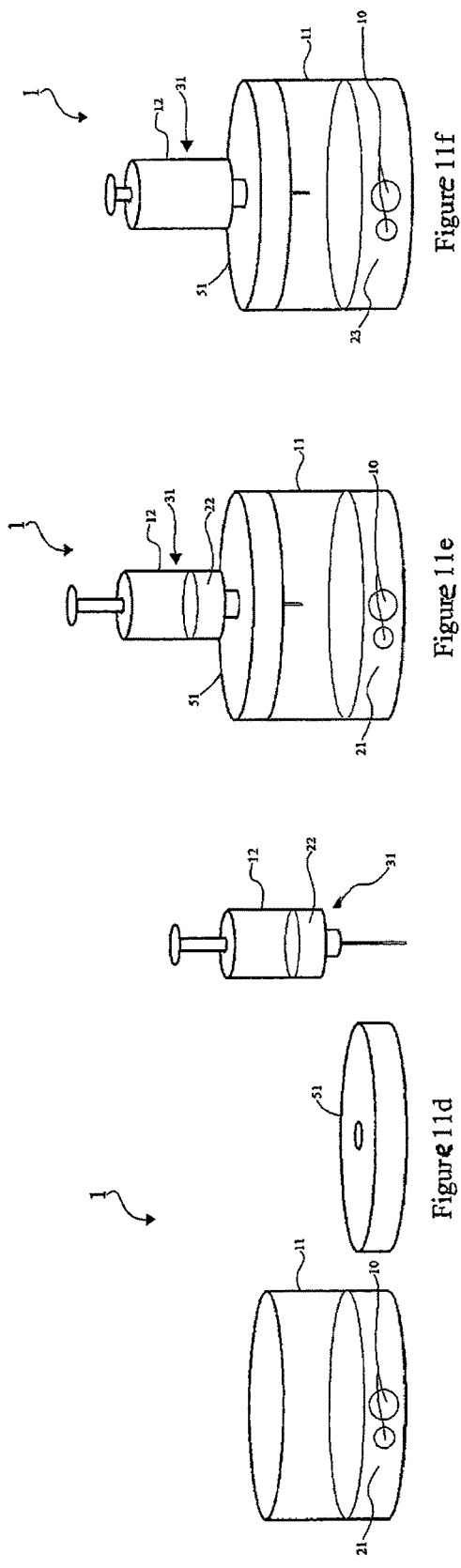

DEVICE AND METHOD FOR COLLECTING, PRESERVING AND/OR TRANSPORTING BIOLOGICAL SAMPLES

This application is a U.S. national stage of PCT/IB2017/056243 filed on 10Oct. 2017 which claims priority to and the benefit of Italian Application No. 102017000051294 filed on 11 May 2017, the contents of which are incorporated herein by reference in their entireties.

STATE OF THE ART

Many of the fixatives used for collecting, preserving and transporting the biological samples have different types of acute and/or chronic toxicity, to the people exposed to them or their vapors.

Among these fixatives there is formalin, which is an aqueous solution of 4% formaldehyde buffered at pH 6.0-8.0 and the main fixative used for the samples of biological tissues, for example withdrawn for diagnostic purpose. It allows stabilizing the, biological tissue and avoiding degradation processes thus allowing their long term preservation; at the same time, the formalin fixation doesn't compromise the analyses to be made on the so-preserved tissue, as it doesn't alter the cellular morphology.

Since at present substitutes of formalin, which provide the same fixation characteristics and at the same time offer cost-efficiency, do not exist, all of the National and International guidelines for the recommendations of how to manage and process the biological samples, are based on it.

Before the recent re-classification of formalin as carcinogenic (UE Regulation 895/2014), in all of the hospital structures, and not only, pre-loaded with formalin containers of different dimensions and volumes (herein below denoted as "conventional containers") have been used for years, so to have the immediate availability of the suitable container at the moment of the tissue sampling, thus avoiding the need to pour the formalin in unsuitable environments, such as for example in ambulatory environment, endoscopic room or operation theatre. In fact, the operator simply opened the container pre-loaded with formalin after the bioptic sampling, inserted the biological sample therein, closed again the pre-loaded container and finally transmitted it to the laboratories appointed to the histological examination.

As already mentioned, recently the formalin reclassification as carcinogenic occurred: this required that health care professionals did not get in contact anymore with the product and vapors thereof in the open environment. In fact, it is accepted using, handling and treating formalin only under adequate chemical hoods. The Ministry of Health issued binding guidelines about the disposal of traditional containers pre-loaded with formalin in the outpatients' clinics and in the operation theatres (LG Ministero della Salute C.S.S. May 2015: Tracciabilità, raccolta, trasporto, archiviazione e conservazione di cellule e tessuti per indagini diagnostiche di Anatomia Patologica—D.Lgs. Apr. 9th 2008 N.81 and s.m.i. Titolo IX Capo II art. 233, 235, 236, 237). The Società Scientifica di Anatomia Patologica (SIAPEC) has drawn up a paper of recommendations addressed to the elimination of the formalin vapors during the collection and transport of histological samples (Linee di indirizzo all'utilizzo della formalina, riclassificata come cancerogena: Linee di indirizzo SIAPEC-IAP Divisione Italiana, February 2016).

All of this implies that it is not possible anymore to open conventional containers in ambulatory environments, endoscopic rooms or surgical units, unless there is the chemical hood. Being practically impossible to equip each of the above mentioned environments with a chemical hood, the interest of the industry concentrated on manufacturing containers that, although pre-loaded with formalin, are designed to avoid the operator contact with the formalin or vapors thereof during the introduction of the tissue sample into the container (herein below, these containers will be denoted as "recent conventional containers"). At the same time, the recent conventional container must allow the easy recovery of the sample at the moment of its analysis, and such a recovery is carried out under chemical hood, for example in an analysis laboratory, in order to analyze the biological sample.

An example of recent conventional container is the container commercially named Biopsafe®: it is a container having a main empty compartment and a cap containing the pre-loaded amount of formalin. The use of the container provides for the operator making the sampling and placing it dry in the main compartment, thus closing the cap and pushing the mechanism pouring the formalin in the main compartment, thus submerging the biological sample.

In addition to Biopsafe®, different variants of said container proliferated in the market. Among these, there are containers equipped with particular mechanisms for pouring the formalin in the empty compartment, for example hourglass mechanisms, or other alternative systems.

A more recent conventional container, which makes use of a technique different from Biopsafe® and variants and however respects the above mentioned safety regulations, provides a container pre-loaded with formalin on which an oily gel floats and prevents the release of vapors. This system doesn't need the formalin to be present in the cap, as the same is already inside the main compartment of the container. However, in practical use the recent conventional containers described above, showed technical problems. For what relates to Biopsafe® and variants:

they do not allow the easy release of the biological sample from the mechanism with which it has been withdrawn (nipper or needle): according to operating practice previous to UE Regulation, in fact said mechanism was dipped and stirred in the formalin contained in the conventional container and therefore the biological sample detached from it easily. It is evident that such a maneuver cannot be carried out by using Biopsafe® and variants, as these containers are not provided with liquid already present in the compartment in which the biological sample is inserted;

the pre-loaded cap assembled on the empty container makes the container instable on the whole, because of the weight almost exclusively concentrated in the upper part. This is generating evident difficulties, such as for example the difficulty to align the various containers on the work plane at the moment of the sampling;

if at the end of the operations, for example at the end of the sampling, the operator forgets to push the release mechanism of the formalin in the main compartment housing the biological sample, the latter dries rapidly and must be considered lost for the histological evaluation, with evident problems and severe inconveniences for the diagnosis;

in case of multiple sampling, a container per each bioptic sample is needed, with an important economic expense. In fact, with Biopsafe® and variants it is not possible to reopen the container after the release of formalin, as the operator would be inevitably exposed to the vapors of the same. Said problems can't be avoided by leaving the biological samples dry in the empty compartment until the completion of the multiple sampling, as the pre-analytic step would be altered in terms of morphology and antigenic preservation. A typical and common multiple sampling is, for example, the gastric biopsy providing three to five bioptic samples: before the UE Regulation, these were collected in a unique conventional container, whereas at present they require three to five recent conventional containers;

the dimensions of Biopsafe® and variants are considerably increased, even doubled, with respect to those of the conventional containers, since both the pre-loaded cap and the main compartment must each contain the whole volume of formalin. This evidently causes a considerable burden on the warehouse storage, with consequent logistic problems.

In the recent bi-phase conventional containers instead, which contain the layer of oily gel above a layer of pre-loaded formalin, the main problems derive from the strong adhesion of the gel to the biological sample, when the latter crosses the oily layer to be dipped in formalin. Furthermore, in said containers difficulties in displaying the biological samples in pathological anatomy often occur when they must be recovered for the histologic processing, and this is particularly manifest for small fragments from bioptic-needle sampling.

Other fixatives comprising toxic volatile components, usually used for the fixation of cells and tissues are, for example, the Carnoy liquid, methacarn, Bouin liquid and fixative B5. Therefore, the operators should avoid as much as possible the exposure to said fixatives, as well as to other fixatives containing toxic volatile components. Considering that the worldwide market is searching for a solution to the problem of managing the formalin, as well as managing many other fixatives noxious to the humans, for example those mentioned above, there is the need to provide alternatives able to solve all of the problems relative to the use of the more recent conventional containers, and in general to the use of noxious fixatives in the open environment, further allowing a convenient and effective management of formalin according to the new safety regulations.

OBJECTS OF THE INVENTION

It is an object of the invention to provide a device for collecting, preserving and/or transporting biological samples, which allows obviating to the multiple problems of the more recent containers.

It is another object of the invention to provide the use of the device according to the invention for collecting, preserving and/or transporting biological samples.

Finally, it is a further object of the invention to provide a method allowing to collect, preserve and/or transport biological samples in the fixatives, for example in formalin, without the exposure of the operator to the noxious components of the fixatives and to the fixatives themselves.

DESCRIPTION OF THE INVENTION

Object of the invention is a device for collecting, preserving and/or transporting biological samples, comprising:
a) a first container which comprises a predetermined amount of substance and/or solution which are harmless and non-noxious to humans (called from now on "first solution"), which is adapted to house said biological samples; and b) a second container comprising a predetermined amount of substance and/or solution which are harmful and noxious to humans (called from now on "second solution").

Said first and second containers may be coupled to each other and said device of the invention further comprises separating means adapted to keep the first solution and the second solution distinct and separate. Furthermore, said first and second containers are configured so that to allow the second solution and first solution to be mixed when said containers are coupled, thus obtaining the fixative "in situ", thanks to a manual action on said containers and/or said separating means.

According to a preferred embodiment, the device of the invention for collecting, preserving and/or transporting biological samples, comprises:
a) a first container which comprises an amount of aqueous solution buffered at pH values from 6.0 to 8.0, preferably from 6.7 to 7.5, between 94% and 98% by weight with respect to the total volume, adapted to house said biological samples; and
b) a second container which comprises an amount of formaldehyde 37% between 2% and 6% by weight with respect to the total volume.

Said first and second containers can be coupled to each other; and said device of the invention further comprises separating means adapted to keep the buffered aqueous solution and formaldehyde distinct and separate. Furthermore, said first and second containers are configured so that to allow the formaldehyde and buffered solution to be mixed when said containers are coupled, thus obtaining the formalin "in situ", thanks to a manual action on said containers and/or said separating means.

In practice, thanks to the device of the invention, the sample withdrawn for the histological or anatomical-pathological examination is placed in the first solution, preferably the buffered aqueous solution that can be handled freely, also in the open environment (i.e., in the absence of chemical fume hood), without any risk for the operator's health, since it is harmless and not noxious. At the same time, the withdrawn sample is dipped in an almost physiological solution and is not subject to any damage, nor any biological alteration, and it is not prone to drying and/or deteriorating. After placing the withdrawn sample in the first solution, preferably the buffered aqueous solution, the device is completed by positioning said first container and coupling it (already comprising the withdrawn sample) to said second container, and finally releasing the second solution thanks to a manual action, preferably formaldehyde, and immediate formation of fixative, preferably formalin, close to the sample itself.

The device according to the invention totally avoids any contact of the human, for example the operator, with the noxious and harmful substances of the fixatives and with the fixatives themselves, for example it avoids any contact with formalin and formaldehyde. In other words, thanks to the device of the invention the operator is completely isolated from the harmful and noxious components of the conventional fixatives, i.e. the second solutions and fixatives themselves, included the vapors thereof. This allows all of the collection, preservation and/or transport operations of biological samples to be completely safe for the operator.

The device of the invention has important advantages with respect to known devices and allows a number of problems arising with the devices of the prior art to be solved. In particular:

it allows placing the withdrawn sample in the completely harmless first solution, thus preventing the operator from breathing, also inadvertently, noxious vapors or exhalations;

it allows an optimal preservation of the sample to be analyzed, the latter being placed by the health care professional directly in the first, almost physiological solution, thus avoiding the risk that the sample spontaneously dehydrates and/or deteriorates by leaving it in a dry environment.

The device of the invention is based on the principle to generate "in situ" the fixative, preferably formalin, once the sample to be examined has been placed in the first solution comprised inside said first container, preferably the buffered aqueous solution constituting about 96% by weight of the total volume of formalin, and once said first container has been coupled to said second container in which there is the second solution, preferably formaldehyde constituting about 4% by weight of the total volume of formalin. By way of example, a container for endoscopic biopsy contains 50 ml formalin: according to a preferred embodiment of the device of the invention, said container for the same purpose will contain about 48 mg buffered solution placed inside the first container, and about 2 mg formaldehyde placed inside the second container.

It is provided for the first container to be opened and tightly closed by the operator, so that to be able to put completely safely one or more biological samples into it. In fact, the first container contains the first solution, preferably a buffered aqueous solution absolutely harmless for the operator's health.

At the moment of use, the biological sample withdrawn by nipper, needle, surgery, or any other means, is introduced in the first container comprising the first solution, preferably the buffered aqueous solution which, as mentioned, doesn't constitute any risk for the operator's health. Therefore, the operator may come in contact with the first solution, preferably the buffered solution, and the vapors thereof without any damage for his health. This freely allows both the rinsing maneuver of the bioptic nipper or needle for the release of the sample, and the collection of multiple bioptic samples before the formaldehyde is added.

Once the biological samples are placed inside the first container, for example at the end of the sampling intervention, the first and second containers are coupled and, thanks to the particular configuration of the device according to the invention as well as its components, by a manual action, for example of the operator, on one or more components of the device, for example on the first container and/or second container, it is possible to mix the first and second solutions, for example by making the second solution flow from the second container to the first container, thus creating the fixative "in situ". This step clearly occur completely safely for the operator, as the occurrence is provided without the operator coming in contact with the second solution and/or fixative, for example with formaldehyde and/or formalin and/or their vapors, for example when the compartment housing the mixing, that can be the first container, is tightly closed. If the interaction with the inside of the first container should be needed more than once, for example in order to insert more biological samples as it happens for multiple samples from the same anatomic site, the first container, which contains only the first solution, preferably the buffered aqueous solution, can be opened and closed more than once without the mixing to occur between the two solutions: it is possible in fact to couple the two containers and mix the two solutions (thanks to manual action) only when necessary, for example at the end of the multiple samples.

The device according to the invention offers surprising advantages with respect to the recent conventional containers, by remedying many of the problems they have. First of all, thanks to the fact that there is the first solution, preferably the buffered solution, in the first container, i.e. that one adapted to house the biological sample, the release of the sample itself is eased by the mechanism with which it has been withdrawn (such as for example a nipper or a needle). Furthermore, the presence of the first solution, preferably the buffered solution, in the container housing the biological sample allows to keep the operational habit to which all of the personnel has been trained to date, i.e. it allows the release of the biological sample in a container comprising a liquid (that until the recently introduced reclassification could have been formalin, whereas in the device of the invention is the buffered aqueous solution). As already stated, obviously there cannot be both of these advantages in the recent conventional containers having the compartment housing the sample that is empty.

Furthermore, the presence of a liquid (the first solution) in the container that must house the biological samples (the first container), allows keeping the static stability of the device of the invention during its use. This also happens in the absence of a lid (i.e., when the first container is opened), exactly as it occurs during the course of a sample. Clearly, recent conventional containers cannot have this advantage having the main compartment empty.

Furthermore, if the operator forgets to mix the two solutions (for example, formaldehyde and buffered solution) after concluding the sampling operations, however the biological samples have high stability margin, as they have been dipped in a para-physiological solution, i.e. the first solution, for example the buffered aqueous solution. Vice versa, as already stated, the dry biological sample inside some of the recent conventional containers has a particularly brief stability margin and therefore is easily damaged.

Still for the reason mentioned above related to the stability of the biological samples, in the case of multiple bioptic samples or similar operations requiring the sampling of several biological samples, the use of several devices of the invention per each bioptic sample is not required, with an evident and important economic saving and simplification of the operational process with respect to some of the recent conventional containers. In fact, thanks to the device according to the invention and to the higher stability conferred to the biological samples by the first solution, preferably the buffered aqueous solution, it is possible to use only one device of the invention per multiple bioptic samples, and it is possible to mix the second solution, preferably formaldehyde, and the first solution, preferably the buffered aqueous solution, only at the end of the operation.

Furthermore, a fundamental advantage still related to the stability of the biological samples in the first solution, for example the buffered aqueous solution, relates to the possibility to completely eliminate the noxious fixatives, for example formalin, from surgical and ambulatory environments, as per the target set by the Italian Ministero della Salute for the next years. In fact, the device of the invention allows: (i) putting the biological sample in surgical and ambulatory environment inside the first container which comprises the first solution, for example the buffered aqueous solution, (ii) tightly closing the first container containing the biological sample by a conventional cap, (iii) sending the first container closed and containing the biological sample, to the location where the analysis takes place, for example in a pathological anatomy laboratory, and (iv) mixing in the laboratory the second solution, for example formaldehyde, thanks to the configuration of the two containers and to a manual action, thus forming in situ the fixative, for example formalin.

A further advantage relates to the overall dimensions of the device of the invention, which remain comparable with those of a conventional container used for the same biological samples. As already stated, most of the recent conventional containers can take twice the space with respect to conventional containers used for the same biological samples. The device of the invention instead, with the same biological sample, comprises the first container that has a volume equal to the volume of a conventional container, and the second container that has a volume much smaller with respect to the total volume of the device of the invention or conventional container, as it must only comprise a small amount of second solution, for example formaldehyde, with respect to the total volume of fixative, for example formalin. This is because the predetermined amounts of the second solution are always much smaller than the predetermined amounts of the first solution. This allows the second container having dimensions comparable, for example, to a cap of a conventional container. Therefore, thanks to the device of the invention, warehousing needs of the structures that need the containers for collecting, preserving and/or transporting biological samples are not modified, thus offering a great advantage from the logistic point of view. Furthermore, it is provided the possibility for the second container of the device according to the invention to be coupled to the first container, and since the containers are not constrained one to each other, the second container can be supplied to the above structure as packages separated from those of the first container. Moreover, there is also the possibility that the packages containing the first container are supplied to a structure, for example the warehouse of the outpatients' clinic, and the packages containing the second container are supplied to another structure, for example the warehouse of the laboratory, with a further advantage from the logistic point of view.

Furthermore, the device of the invention also has advantages over the recent conventional bi-phase containers: since there isn't any oily gel or other oily surface liquids in the device of the invention, there won't be the critical issues of their possible adhesion to the biological samples, thus making easy and quick the deposit and recovery of the same into and from the device according to the invention.

According to a preferred embodiment the second container, preferably comprising formalin in the amounts above, is a lid allowing the first container to be opened and tightly closed, preferably comprising buffered aqueous solution in the amounts above, for example the second container is a threaded lid, such as a threaded plug or screw cap. According to a further preferred embodiment, there is a further lid adapted for opening and tightly closing the first container.

According to the latter preferred embodiment, the first container is used in the sampling step of one or more biological samples together with the further lid, which allows the first container to be opened and tightly closed. The second container, that can be used to tightly close the first container, is riot used until the mixing of the two liquids must occur, for example at the end of the sampling operations. Therefore, during this sampling step, the first container can be freely opened and closed by the operator by means of the further lid, without any damage for his health and without any mixing between the two solutions, preferably the buffered solution and formaldehyde, with consequent formation of fixative, preferably formalin. When there is the need to form the fixative, preferably formalin, for example once the sampling step is concluded and the one or more necessary biological samples are placed in the first container, the operator shouldn't do anything else than closing the first container by using the second container, which can be coupled to one another, and the two solutions are kept separate and distinct thanks to the separating means. Thanks to a manual action of the operator, such as for example screwing the second container on the first container, the mixing of the two solutions occurs, preferably the transfer of the second solution occurs, preferably formaldehyde, from the second container to the first container, thus forming the fixative, preferably formalin.

This preferred embodiment offers further advantages, thus resulting even more useful for collecting, preserving and/or transporting biological samples with respect to the conventional more recent containers.

First of all, this preferred embodiment is that one allowing to mostly adhere to the operational habit to which the operators have been trained and used to. In fact, this preferred embodiment is departing from the recovery operation of biological samples with the conventional containers only for the use of a second lid. In other words, according to this preferred embodiment, the operator is departing from the operational habit only for the use of the second container to close the first container at the end of the operations, and the remainder of the operational procedure remains identical to the operational procedure prior to the formalin reclassification.

Furthermore, this preferred embodiment can provide for the second container to be made of a different color, for example red, with respect to the further lid, that for example is blue. This allows an immediate visual evidence of the fact that the fixing has occurred and provides a clear indication of which device according to the invention must be exclusively opened under the hood, i.e. the device of the invention having the lid of a given color, for example red, as it contains fixative, for example formalin. Furthermore, the operator that should forget to mix the two solutions, for example formaldehyde and buffered solution, after having concluded the sampling operations, thanks to the color of the two lids is able to easily and immediately realize the forgetfulness and accordingly to remedy to it.

Therefore, this preferred embodiment facilitates all of the recovery and transport operations of biological samples, by minimizing the possible mistakes of said operations and providing at the same time a simple and effective solution, as it is safe, to the problems about the management of noxious fixatives, for example formalin, and vapors thereof.

Furthermore, it is an object of the present invention the use of the device of the invention according to any of its embodiments, for collecting and/or preserving and/or transporting biological samples.

It is a further object of the present invention a method for collecting, preserving and/or transporting biological samples which comprises:
a) putting said biological samples in a predetermined amount of a first solution; and
b) mixing a predetermined amount of second solution to said first solution of step a), thus forming the fixative.

A preferred embodiment of the method according to the invention is a method for collecting, preserving and/or transporting biological samples which comprises:
a) putting said biological samples in an amount of aqueous solution buffered at pH from 6.0 to 8.0, preferably from 6.7 to 7.5, from 94% al 98% by weight with respect to the total volume; and b) mixing an amount of formaldehyde, from 2% to 6% by weight with respect to the total volume, to said buffered aqueous solution of step a), thus forming formalin.

The method of the invention obviously will have all of the advantages described for the device according to the invention. Note that step b) can be carried out in different locations with respect to where step a) is carried out, for example: step a) can be carried out in surgical or ambulatory environment, and step b) can be carried out in analysis laboratory.

Another embodiment of the method of the invention provides the use of the device of the invention according to any embodiment thereof. Therefore, the method of the invention for collecting, preserving and/or transporting biological samples may comprise:

a) putting said biological samples in the first container of the device of the invention comprising a predetermined amount of first solution, preferably an amount of aqueous solution buffered at pH from 6.0 to 8.0, preferably from 6.7 to 7.5, from 94% to 98% by weight with respect to the total volume; and b) mixing said first solution of step a), preferably said buffered aqueous solution, with a predetermined amount of second solution, preferably an amount of formaldehyde from 2 to 6% by weight with respect to the total volume, thus forming said fixative, preferably formalin; in other words, allowing the mixing of the second solution, preferably formaldehyde, with the first solution, preferably the buffered aqueous solution, thus forming the fixative, preferably formalin, following a manual action on the first container and/or second container and/or separating means.

Also in this case, step b) can be carried out in different locations with respect to where step a) is carried out.

According to a preferred embodiment of the method of the invention, said mixing is obtained thanks to the passage of the second solution, preferably formaldehyde, placed inside the second container, in the first container, thus forming the fixative, preferably formalin.

It is evident that the method of the invention can use any embodiment of the device of the invention.

DESCRIPTION OF THE FIGURES

Further aspects and advantages of the present invention will be clearer from the following description, that is made by way of illustration and not limitation, with reference to the attached schematic drawings, wherein.

Figure 3:
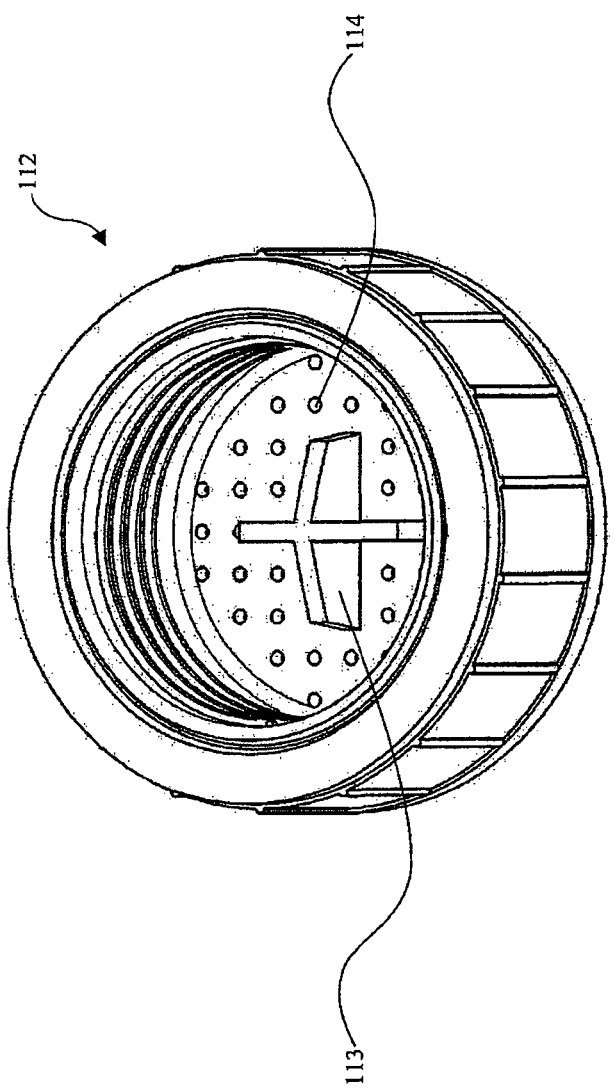
Figure 4:
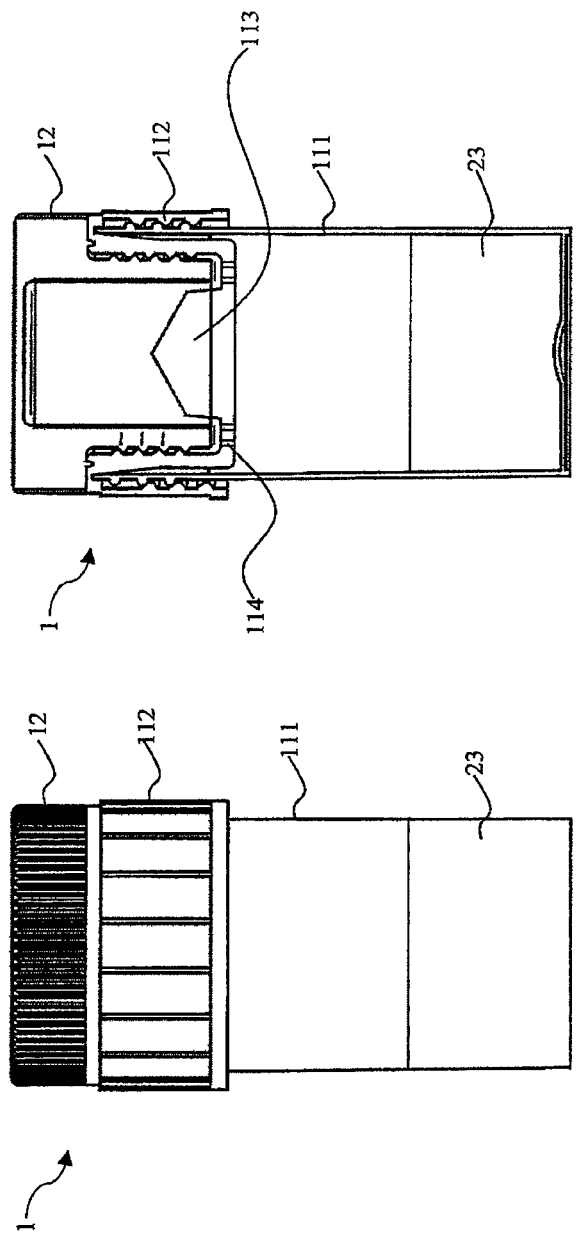
Figure 5:
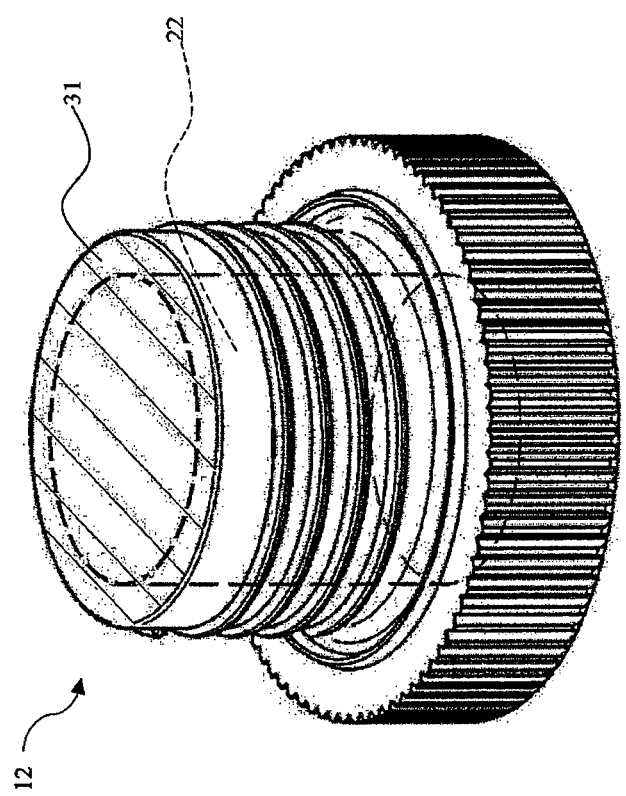
Figure 6:
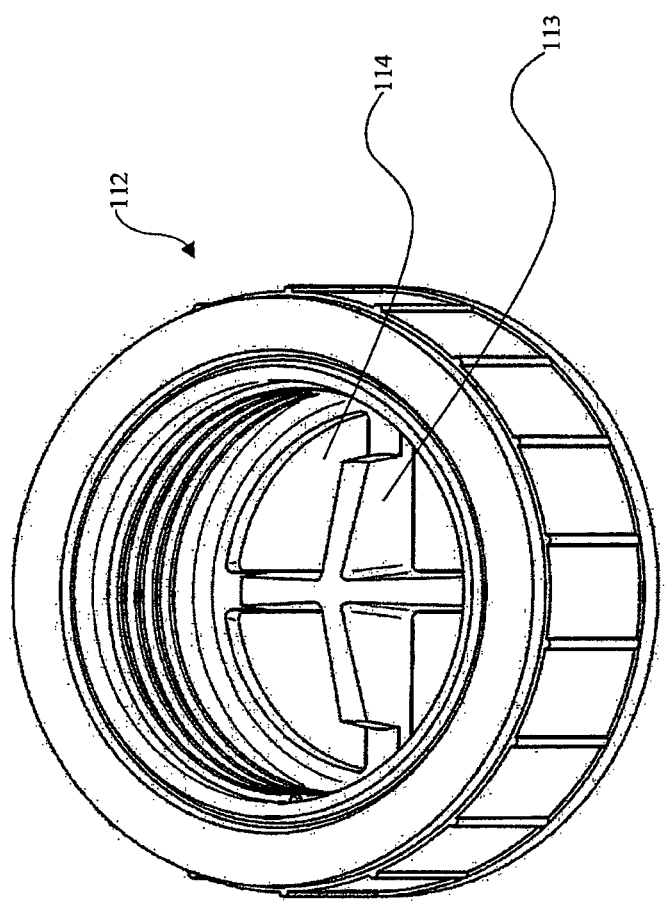
Figure 7:
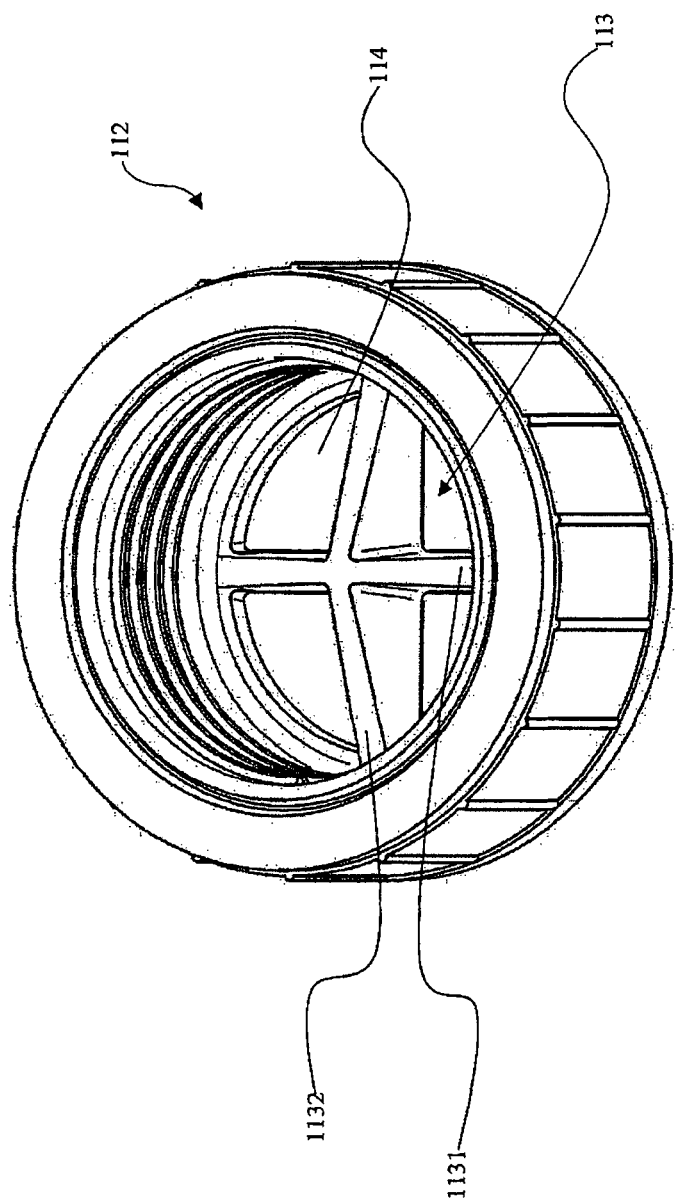
Figure 9A:
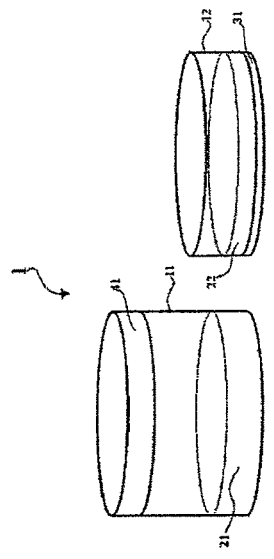
Figure 9B:
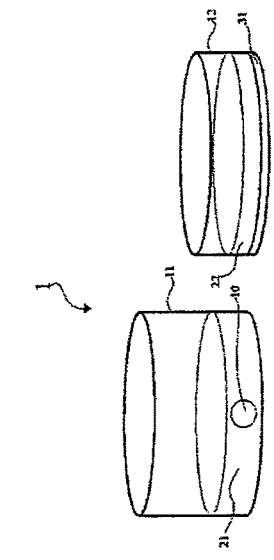
Figure 9C:
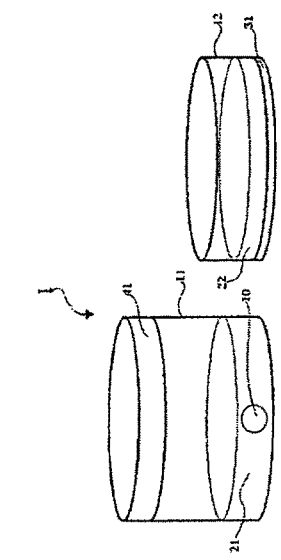
Figure 9D:
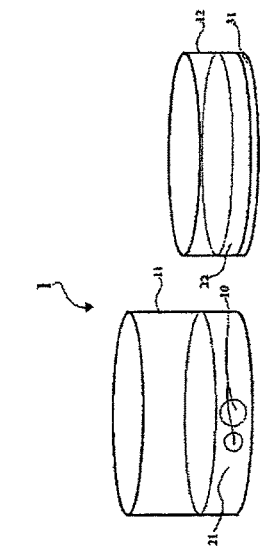
Figure 9E:
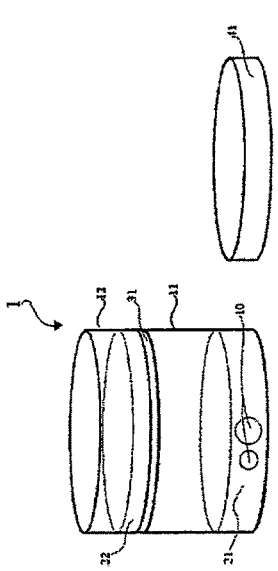
Figure 9F:
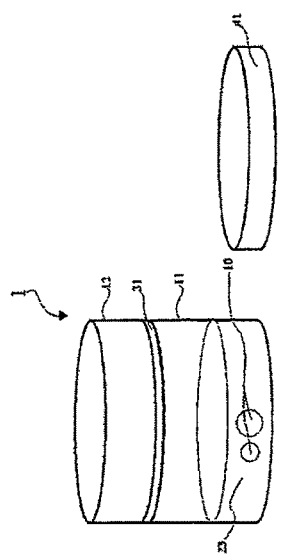

Figures from FIG. 2 to FIG. 8 depict different elements and/or details of a particularly preferred embodiment:

FIG. 2 shows the first container according to said particularly preferred embodiment;

FIG. 3 shows part of the first container according to said particularly preferred embodiment;

FIG. 4 shows the device of the invention according to said particularly preferred embodiment;

FIG. 5 shows the second container and the separating means according to said particularly preferred embodiment;

FIG. 6 shows a detail of part of the first container according to still another particularly preferred embodiment;

FIG. 7 shows another detail of part of the first container according to a further particularly preferred embodiment; and FIG. 8 shows the differences among recent conventional containers and the first container/device according to said particularly preferred embodiment.

FIG. 9 is a schematic representation of the device according to a preferred embodiment.

FIG. 10 is a schematic representation of the device according to a further embodiment.

FIG. 11 is a schematic representation of the device according to another embodiment.

Figure 1C:
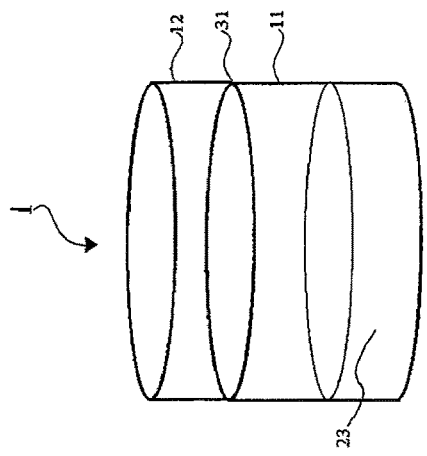
FIG. 1 is a schematic representation of the device of the invention.
Figure 1B:
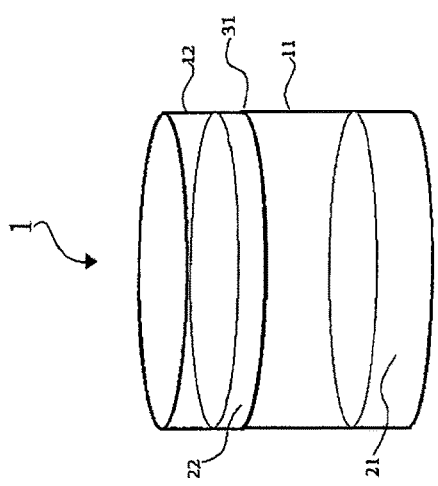
Figure 1A:
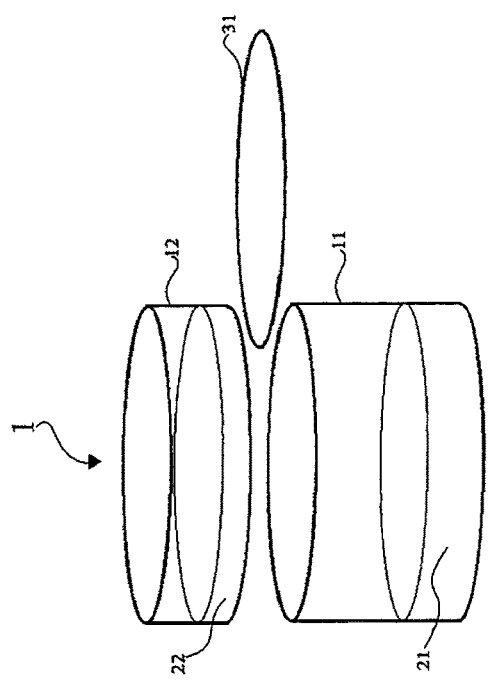

FIG. 1a shows the device 1 for preserving and/or transporting biological samples 10 comprising:

i) a first container 11 which comprises a predetermined amount of a first solution 21, preferably in an amount of aqueous solution buffered at pH values from 6.0 to 8.0, preferably from 6.7 to 7.5, between 94% and 98% by weight with respect to the total volume of formalin, adapted to house said biological samples; and ii) a second container 12 which comprises a predetermined amount of second solution 22, preferably an amount of formaldehyde between 2% and 6% by weight with respect to the total volume of formalin;

said first and second containers can be coupled to each other; said device 1 further comprises separating means 31 adapted to keep the two solutions 21 and 22, preferably the buffered solution and formaldehyde, distinct and separate; said first and second containers being further configured so that to allow the second solution 22, preferably formaldehyde, and the first solution 21, preferably buffered solution, to be mixed when said containers are coupled, thus forming said fixative 23, preferably formalin, "in situ", thanks to manual actions on said containers and/or said separating means 31.

In the present invention, by "first solution" is meant a substance and/or solution represented by the harmless and not noxious components of conventionally used fixatives. In other words, said first solutions do not cause any acute and/or chronic toxicity to humans, and generally their safety data sheets and/or labels and/or those of their components do not have hazard pictograms related to risks noxious to human health, such as for example the "Globally Harmonized System of Classification and Labelling of Chemicals" GHS05, GHS06, GHS07 and GHS08 hazard pictograms.

By way of example, the first solution is a buffer or brine of salts that are not noxious and/or nor volatile, such as sodium chloride or sodium acetate, preferably the first solution is the buffered aqueous solution.

In the present invention, by "buffered aqueous solution" or "buffered solution" is meant the solution conventionally used for making the formalin, constituting about 96% by weight with respect to the total volume of formalin. Said buffered solution generally comprises phosphate buffer about 0.05 M, in turn constituted by monosodium phosphate ($NaH_2PO_3$) from about 0.15% to about 0.20% by weight with respect to the total volume and disodium phosphate ($Na_2HPO_3$) from about 0.70% to about 0.80% by weight with respect to the total volume, possibly methanol about 0.1% by volume with respect to the total volume and water q.s. In the present invention, by "second solution" is meant a substance and/or solution that are represented by the harmful and noxious components of the conventionally used fixatives. In other words, said second solutions are the components of the fixatives conventionally used that cause acute and/or chronic toxicity to humans by the exposure to those, for example by the exposure to their vapors, said second solutions, and/or some components of said second solutions, being usually volatile. Generally, the safety data sheets and/or labels of said second solutions, and/or those of their components, have one or more hazard pictograms, such as for example the "Globally Harmonized System of Classification and Labelling of Chemicals" GHS05, GHS06, GHS07 and/or GHS08 hazard pictograms. By way of example, the second solution can be formaldehyde, mercury chloride or chloroform, in solution or as such substance.

The predetermined amounts of the first and second solutions are the amounts allowing, when mixed, the formation of a fixative, for example formalin, having a titre conventionally used for any application concerning collecting, preserving and/or transporting biological samples. Such amounts will vary based on the type of fixative to be used and/or titre of said fixative to be used and/or type of biological sample and/or type of analysis on the biological sample. By way of example and preferably, the fixative at issue is formalin, accordingly: the first solution is an aqueous solution buffered at pH values from 6.0 to 8.0, preferably from 6.7 to 7.5, and its predetermined amount is between 94% and 98% by weight with respect to the total volume of formalin; whereas the second solution is formaldehyde and its predetermined amount is between 2% and 6% by weight with respect to the total volume of formalin.

The first solution, the second solution and the predetermined amounts of the first and second solutions of each conventionally used fixative (such as for example formalin, Carnoy liquid, methacarn, Bouin liquid and fixative B5), are obviously well known to the technician in the art.

In the present invention, two containers may be "coupled" means that the two containers can be joined and/or coupled and/or linked, thus constraining them in a detachable way to each other; for example by threaded portions.

In the present invention, by "separating means" is meant any mechanism and/or tool and/or generic material interposed between the two containers and/or two liquids comprised in the two containers and that avoids the mixing of the two liquids comprised in the two containers, i.e. to keep them distinct. These separating means can comprise one or more impermeable membranes, ducts or holes with capillary dimensions that are not allowing the passage of liquids by capillarity, systems allowing not to make the liquids flowing thanks to pressure differences, for example thanks to the vacuum, combinations thereof, etc., and are known to the skilled in the art.

Said first and second containers are configured to be able to mix the two liquids, preferably by allowing the passage of the second solution, preferably formaldehyde, from the second container to the first container, following a manual action, for example made by the operator, on said first container and/or second container and/or separating means. Such arrangements are known in the art and can comprise for example mechanisms which make use of impermeable membranes and means perforating them, that can be operated thanks to manual actions such as for example the screwing or applying a pressure on one or more components. For example, the impermeable membrane could constitute the separating means, and the manual action on said first container and/or second container and/or separating means would allow its perforation. Accordingly, by "manual action" in the present invention is meant an action, such as for example a screwing action or an action of making pressure, performed by an individual, for example the operator, on one or more from the first container, the second container and the separating means. Said manual action is an action allowing the mixing of the two solutions comprised in the containers of the invention, thanks to the configuration of said first and second containers. The whole device 1 of the invention is further configured so that to never expose the operator to the second solution 22, preferably formaldehyde, and/or to the fixative 23, preferably formalin, and/or their vapors; accordingly said first and second containers are configured so that to be able to mix the two solutions and thus form the fixative 23, preferably formalin, inside tightly closed compartments, for example inside the first tightly closed container 11.

It is provided for said first container 11 to be opened and tightly closed by the operator, for example by a lid, such as a threaded plug or a screw cap.

Said separating means 31 can be constrained to one or both the containers, for example to the second container 12, and can be integrated and/or integral to one or both containers.

The dimension of the first container 11 and the predetermined amount of the first solution 21, preferably buffered aqueous solution, are a function of the volume of the biological samples 10 the first container 11 has to house, therefore the predetermined amount of the second solution, preferably formaldehyde 22, and the dimension of the second container 12 will depend in turn by the volume of the biological samples. By way of example, bioptic samples usually require a biological samples/formalin volume ratio of about 1:50. In this case, the first container 11 could be at least about 50 times bigger than the biological samples 10, and the second container 12 is provided for having dimensions suitable to contain the correct predetermined amount of second solution, for example formaldehyde (i.e., from 2% to 6% by weight with respect to the total volume of formalin). For the just explained reason, it is clear that the device 1 of the invention is provided for being of different shape and dimensions. In FIG. 1 it is possible to schematically see the device 1 of the invention. More precisely, in FIG. 1a it is possible to see: the first container 11 comprising the first solution 21, preferably buffered aqueous solution, the second container 12 comprising the second solution 22, preferably formaldehyde, and the separating means 31. In FIG. 1b it is possible to see the coupling of the two containers and the separating means 31, which do not allow the mixing of the first solution 21, preferably the buffered aqueous solution, comprised in the first container 11 with the second solution 22, preferably formaldehyde, comprised in the second container 12.

Finally, in FIG. 1c it is possible to see that the mixing of the second solution 22, preferably formaldehyde, with the first solution, preferably buffered aqueous solution, has taken place thanks to the presence of the fixative 23, preferably formalin, inside the device 1 of the invention, following a manual action.

A particularly preferred embodiment of the device of the present invention is shown in the different aspects thereof in FIGS. 2 to 8, and provides for:

said first container 11 consisting of:
  a reservoir 111 containing said first solution 21 and adapted to house said biological samples; and
  a female cap 112 comprising puncturing means 113; and
said second container 12 is a male cap comprising the separating means 31; said female cap 112 can be coupled both to said reservoir 111 and said male cap, thus allowing the fluid connection between said reservoir 111 and said male cap.

In particular, said fluid connection is preferably carried out by means of one or more holes 114 that are on said female cap 112, each having a surface that doesn't allow the interlocking of said biological samples 10 therein. More preferably the surface of each of said one or more holes 114 can vary, and for biological samples of small dimensions can be of about 0.05 mm$^2$ or more, whereas for samples of bigger dimensions can be of about 1 cm$^2$ or more. It is evident that such a surface can vary depending on the dimension of the biological sample to be preserved and transported, and therefore it is important that each of the one or more holes 114 have a sufficiently big surface so as not to allow the interlocking of said biological samples, any dimension they would be. Furthermore, said one or more holes 114 are preferably circular sector openings.

Still according to the present particularly preferred embodiment, said puncturing means are preferably a cross punch, and more preferably said cross punch consist of two partitions intersecting one to the other (1131 and 1132) and that each join two distinct points of the circumference of said female cap 112.

In the present particularly preferred embodiment, said separating means 31 is an impermeable membrane that can be perforated. By way of example, in the present particularly preferred embodiment, said separating means is an aluminum foil.

Furthermore, still according to the present particularly preferred embodiment, said second container 12 is preferably thermo-sealed by said separating means 31, for example by said aluminum foil. Therefore, the separating means 31 of the present particularly preferred embodiment also perform the function of tightly closing the second container 12, as depicted in FIG. 5.

The coupling of said female cap 112 to said reservoir 111 and said male cap is possible, for example, by threaded portions that are on all of the three above mentioned elements, thus allowing said female cap 112 to be screwed to said reservoir 111, and said male cap to said female cap 112. The coupling of the three elements mentioned above (depicted in FIG. 4) allows the tight closing of said device 1 and the fluid connection between the reservoir 111 (which is part of the first container 11) and the male cap (which, in the present particularly preferred embodiment, corresponds to the second container 12). Furthermore, the coupling of said second container 12 (male cap) to said female cap 112, for example by screwing, allows the perforation of the separating means 31 comprised in said second container 12 (according to the present particularly preferred embodiment) by means of the puncturing means 113: in fact the screwing can be considered the manual action that allows the mixing of the first and second solutions, thus forming the fixative liquid, preferably formalin, in situ, i.e. in the reservoir 111. Therefore, the puncturing means 113 perforate the separating means 31 following the coupling of the female cap 112 to the male cap, and the second solution is poured inside the reservoir 111, which contains the first solution 21 and the biological sample. The fluid connection between said reservoir 111 and said male cap is allowed by the fact there are one or more holes 114 on said female cap 112, as depicted in FIG. 3. It has been noticed that in many recent conventional containers of known type the size of the possible holes, which allow the contact between biological sample and fixative solution, is a critical factor for the preservation and transport of the biological samples. In fact, it has been observed that a high number of circular holes, each being of small diameter, allows a rapid descent of formalin inside the main compartment and, at the same time, it is not allowing the biological samples of small dimensions to enter in the cap initially containing formalin. However, it has been noticed that the biological samples of small dimensions can interlock inside the above mentioned holes with small diameter: when this occurs, the biological sample doesn't remain in contact with the fixative solution (i.e., it remains "dry"), thus undergoing an inadequate preservation and providing unreliable or adulterated analytical results. The operator is therefore obliged to carry out another bioptic sample on the patient, with consequent additional costs and further inconveniences for the patient. Notwithstanding such critical issues, the total surface of the holes must be sufficiently wide to allow the rapid and total pouring of the fixative inside the main compartment, in order to be able to rapidly and promptly fix the biological sample, when desired.

The critical issues of the recent conventional containers described above raise the need to find an alternative way that makes quick and complete the mixing of said two solutions of the device of the present invention and, at the same time, doesn't allow the interlocking or loss of the biological sample inside the device itself, for example inside the one or more holes. It has been found that when the fluid connection between first and second containers is carried out by means of one or more holes each having a surface not allowing the interlocking of said biological samples 10 therein, preferably a surface that can be of about 0.05 mm$^2$ or more, or also about 1 cm$^2$ or more. With such surfaces, also the biological samples of smaller dimensions do not remain interlocked inside them. Furthermore, it has been found that when said one or more holes are circular sector openings (as shown in FIG. 6), following the manual action, a rapid and complete descent of the second solution 22 inside the reservoir 111 is occurring, without the biological samples 10 are interlocking inside the one or more holes 114. In fact, the circular sector opening and/or a surface as described above for each of the one or more holes 114 allows the biological samples 10 of small dimensions to freely raise inside the second container 12 and to freely return in the same way in the reservoir 111, without being blocked or interlocked inside the device of the invention. Accordingly, the surface and/or type of the one or more holes 114 described above allow rapid mixing between the first and second solutions, not allowing the biological samples, any dimension they should have, interlocking or blocking inside said holes.

The puncturing means 113 can advantageously be a cross punch. In fact the cross punch is useful, easy to be produced, reliable and provides constant and reproducible holes. Preferably, said cross punch is constituted by two partitions intersecting one to the other (1131 and 1132) and each joining two distinct points of the circumference of said female cap 112, as shown in FIG. 7. In other words, in its preferred embodiment, the partitions of said cross punch are as long as to coincide with the circumference of the female cap 112. This allows to efficiently perforate the separating means 31 that can preferably be an aluminum foil.

In the present particularly preferred embodiment, there is further an impermeable and adhesive removable film 115 adapted to contain said first solution 21 inside said first container 11, said removable film 115 adhering to said female cap 112 as shown in FIG. 2. The removable film 115 will be removed prior to the coupling of the second container 12 to the female cap 112. Such a removable film 115 has the function to tightly close said first container 11, in the present particularly preferred embodiment consisting both of the reservoir 111 and the female cap 112. This is ensuring an important advantage to the device of the invention according to the present particularly preferred embodiment: the possibility to uncouple the first and second containers still keeping both said containers tightly closed (remember that, according to the present particularly preferred embodiment, the second container is tightly closed by the separating means). There can be such an advantage also in other embodiments of the present invention. The recent conventional containers, while not being constrained in any of their parts, do not allow the uncoupling between the main compartment and the compartment containing the fixative solution (for example, cap) without at least one of the two compartments being opened. The device of the invention instead, and in particular the present particularly preferred embodiment, provides for the possibility to separate the compartment housing the biological sample (i.e., the first container 11) from the compartment containing the noxious solution (i.e., the second container 12), thus keeping both the containers tightly closed. This provides great advantages from the logistic point of view: as already stated, it is possible to provide, for example, the first container 11 to the sampling room of the biological sample, and the second container 12 to the analysis laboratory. It can be understood that the first container 11, being harmless in all of its components, could be handled and/or transported without particular precautions and without any application to it of pictograms for the chemical risk or danger. Such a possibility cannot occur with the recent conventional containers: the compartment housing the biological sample must always be transported together with the compartment containing the noxious liquid (for example, the cap), otherwise one of the two compartments (in general, that one housing the biological sample) will stay open, and therefore could not be handled without the other compartment tightly closing the whole container (as, for example, the opened compartment is subjected to external contaminations). Not only: being able to uncouple the two containers 11 and 12 keeping them tightly closed also provides a further advantage from the safety point of view: as already stated, when the first container is uncoupled from the second container (as in FIG. 2), it can be opened in the absence of fume hood, since inside it there is exclusively the first (harmless) solution. Vice versa, if the first and second containers are coupled (as in FIG. 4), the device of the invention must exclusively be opened under a fume hood, since the fixative liquid, preferably formalin, is in the compartment of the biological sample. It is evident that there is a clear visual difference among the first container (as depicted in FIG. 2) and the coupled first and second containers (as depicted in FIG. 3): this difference (that can be observed from FIGS. 8c and 8d) will allow the operator to understand at first sight which device could be freely opened and handled, and which device could not be. For the recent conventional containers this occurs differently, as it can be observed from FIGS. 8a and 8b: it is difficult to visually recognize a recent conventional container to be freely opened everywhere from a recent conventional container to be opened exclusively under a hood, as both are always and however constituted by the same parts. FIG. 8 schematically shows the visual differences among two recent conventional containers and two devices of the invention; the containers or devices that can be freely opened are those where there isn't noxious fixative, for example formalin, inside the compartment housing the biological sample (FIGS. 8a and 8c), vice versa the containers or devices that can be opened under a fume hood are those wherein there is noxious fixative, for example formalin, inside the compartment housing the biological sample (FIGS. 8b and 8d).

A collecting, preserving and/or transporting method using the device according to the present particularly preferred embodiment is the following: the operator put the biological sample 10 inside the reservoir 111 that is part of the first container 11.

This occurs thanks to the uncoupling between reservoir 111 and female cap 112 (that can be carried out by unscrewing the female cap 112 from the reservoir 111). Once the biological sample 10 is put inside the reservoir 111, the operator can couple the female cap 112 to the latter and thus achieve a tightly closed first container 11 (in fact, notwithstanding the one or more holes 114 that are on the female cap 112, the first solution 21 cannot exit from the first container 11 thanks to the removable film 115, as well as thanks to the threaded portions that are on the reservoir 111 and female cap 112). When needed, for example in the analysis laboratory or a few moments after the coupling of the reservoir 111 to the female cap 112, an operator can remove the removable film 115 and can couple (by screwing) the second container 12 (the latter being a male cap in the present particularly preferred embodiment) to the female cap 112 (the coupling occurs by means of threaded portions that are on both elements). Such a screwing is the manual action allowing the mixing of the first solution 21 and second solution 22. In fact, the screwing allows the perforation of the separating means 31 (in this particularly preferred embodiment, comprised in the second container 12) by means of the perforating means 113 comprised in the female cap 112 and the consequent pouring of the second solution 22 inside the reservoir 111, thus forming in situ the fixative 23. The mixing of the first and second solutions is eased thanks to the fluid connection between first container 11 and second container 12, the fluid connection being allowed by the one or more holes 114 that are in the female cap 112.

Figure 2B:
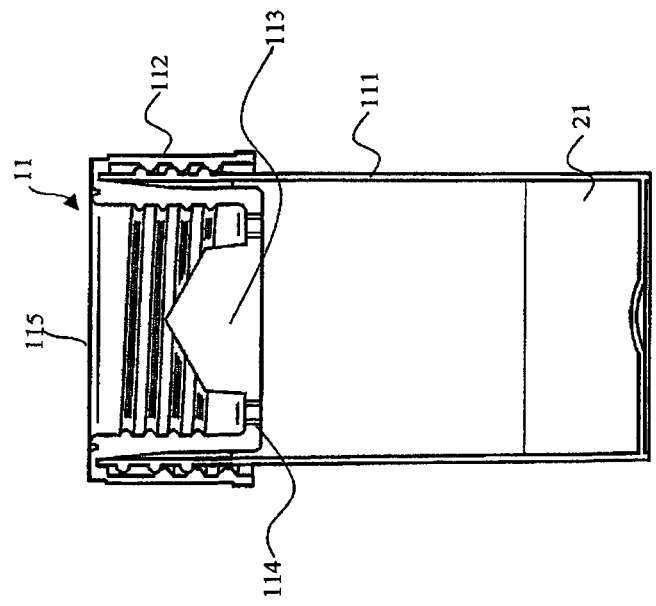
Figure 2A:
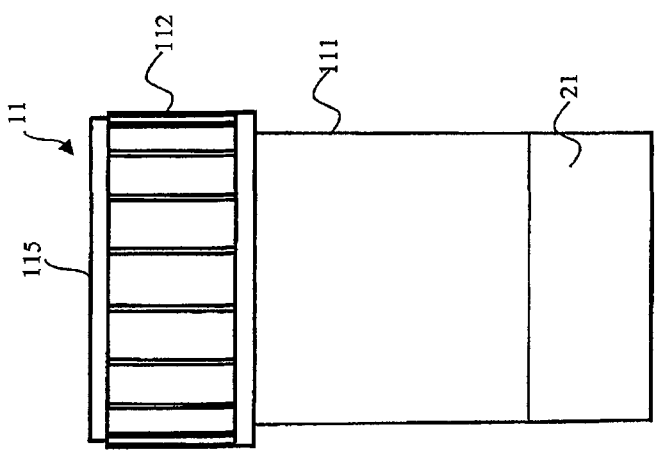

FIG. 2 shows the first container 11 according to a particularly preferred embodiment of the device of the invention. In particular, FIG. 2a shows the reservoir 111 (containing the first solution 21) coupled to the female cap 112, both being elements that constitute the first container 11 according to the present particularly preferred embodiment. FIG. 2b, a front section of FIG. 2a, shows the reservoir 111 (containing the first solution 21) coupled to the female cap 112 (by means of threaded portions), the puncturing means 113 that are on the female cap 112 (useful for perforating the separating means 31, not shown in the present Figure, following a manual action) and the one or more holes 114 allowing the fluid connection between the reservoir 111 and the second container 12 (the latter not shown in the present Figure). In both FIG. 2a and FIG. 2b, the first container 11 is tightly closed by means of a removable film 115 adhering to the female cap 112. Such removable film 115 will be removed when there must be a coupling between the second container 12 (male cap, not shown in the present Figure) and the female cap 112.

FIG. 3 shows in detail the female cap 112. In particular, it is possible to see the puncturing means 113, the threaded portions useful to couple said female cap 112 to the second container 12 (not shown in the present Figure), and the one or more holes 114 allowing the fluid connection between the reservoir 111 and the second container 12 (not shown in the present Figure). The removable film 115 is not shown in the present Figure.

FIG. 4 shows the device 1 of the invention according to a particularly preferred embodiment thereof. In particular, in FIG. 4a it is possible to see the first container consisting of reservoir 111 and female cap 112 and coupled to the second container 12, in the present particularly preferred embodiment being in the form of a male cap.

FIG. 4b is the front section of FIG. 4a and shows: the puncturing means 113, the one or more holes 114 (useful to fluidically connect the second container 12 (male cap) to the reservoir 111), the coupling between reservoir 111 and female cap 112 and between female cap 112 and male cap (second container 12), and the fixative 23, preferably formalin. The coupling of the second container 12 to the first container eased the mixing of the first solution 21 and second solution 22 (which are not shown in the present Figure), thus forming "in situ" a fixative 23, preferably formalin, thanks to the perforation of the separating means 31 (not shown in the present Figure) by the puncturing means 113 (shown in FIG. 4b) following the manual screwing action of the second container 12 in said female cap 112.

FIG. 5 shows in detail the second container 12 which, in the present particularly preferred embodiment, is in the form of male cap. In particular, FIG. 5 shows the second solution 22 (dashed, contained inside said male cap), the threaded portions of the second container 12 (which allow the coupling of the latter to the female cap 112, not shown in the present Figure), and the separating means 31, in this particularly preferred embodiment being useful also to tightly close the second container 12: in fact such a container 12 is thermo-sealed by said separating means 31, which can advantageously be an aluminum foil that can be perforated.

FIG. 6 shows a preferred embodiment of the female cap 112 forming the first container 11. In the present Figure it is possible to see the puncturing means 113 and the one or more holes 114 with circular sector opening. This type of holes is advantageous as it allows a cross punch to be used as a puncturing means 113 (as depicted in the present Figure), and at the same time doesn't allow the interlocking of biological samples, any dimension they should be, inside the one or more holes 114. In particular, the samples of small dimensions will freely pass through the one or more holes 114 without interlocking therein, whereas the samples of bigger dimensions will not pass through them and will remain confined in the reservoir 111 (not shown in the present Figure).

FIG. 7 shows another preferred embodiment of the female cap 112, which has a cross punch as puncturing means 113, said cross punch consisting of two components intersecting to one another. (1131 and 1132) and each joining two distinct points of the circumference of said female cap 112.

FIG. 8 shows the visual difference among recent conventional containers that can be freely opened or that cannot be freely opened, and devices of the invention according to a particularly preferred embodiment that can be freely opened or that cannot be freely opened. In particular, FIG. 8a shows a recent conventional container that can be freely opened, i.e. in the absence of fume hood, as in the compartment housing the sample 13 there isn't the formalin 24 (noxious volatile liquid). FIG. 8b shows a recent conventional container that cannot be freely opened, i.e. it can be opened exclusively under a fume hood, as in the compartment housing the sample 13 there is the formalin 24. By comparing FIG. 8a with FIG. 8b, note that the two containers cannot easily be distinguished from one another, as both consist of all the components constituting the container itself, i.e. the compartment housing the biological sample 13 and the cap containing the formalin 14 (the same formalin that will then be poured in the compartment housing the biological sample). The only difference among the recent conventional containers in FIG. 8a and in FIG. 8b is that there is or there isn't formalin 24 inside the compartment housing the biological sample 13. Therefore, an operator is able to easily recognize if the container could be handled without many formalities (i.e., the container in FIG. 8a), or else if the container must be handled under a fume hood (i.e., the container in FIG. 8b). In FIG. 8c it is shown the first container 11 of the device of the present invention 1 according to a particularly preferred embodiment thereof. In particular, from this Figure it is possible to note the reservoir 111 and the female cap 112 that constitute the first container 11 according to the present particularly preferred embodiment. The first container 11 can be freely opened, i.e. in the absence of fume hood: it is used as shown schematically in FIG. 8c, for example, to collect the biological sample when doing the bioptic sampling, without the aid of further components. In fact, it is tightly closed thanks to the coupling between female cap 112 and reservoir 111, and thanks to the removable film 115, and therefore the biological sample can be preserved for a finite time inside the first container 11. In FIG. 8d the device of the present invention 1 according to a particularly preferred embodiment thereof is shown; in particular, it is possible to note the reservoir 111, the female cap 112 and the male cap (the latter being the second container 12 of the invention). The device 1 of the invention depicted in FIG. 8d cannot be freely opened, i.e. it must be opened under a fume hood: in fact, the coupling of the second container 12 to the first container 11 (in this particularly preferred embodiment, formed by the coupling of reservoir 111 and female cap 112) caused the rupture of the separating means, with the consequent mixing of second solution and first solution 21, forming the fixative 23 in situ. By comparing the FIG. 8c with FIG. 8d, note that the two devices depicted in Figures can be promptly distinguished at first sight: in the device of FIG. 8d there is one additional component (i.e., the male cap 12). Such a component can conveniently be of a color different from the female cap 112, so that to further increase the visual difference between the devices of FIGS. 8c and 8d. As already stated, this difference considerably improves the safety and facilitates the workflow of the operators, mainly if they have to, for example, analyze a high number of biological samples.

FIG. 9 shows a preferred embodiment of the invention, in which said second container 12 comprising the second solution 22, preferably formaldehyde, is a lid allowing the first container 11 to be opened and tightly closed. In this preferred embodiment, the device 1 of the invention comprises a further lid 41 adapted to open and tightly close the first container 11. In FIG. 9a it is possible to see the device 1 of the invention which comprises the first container 11 comprising the first solution 21, preferably buffered solution, which is tightly closed by the further lid 41. Apart from this, it is possible to see the second container 12 comprising the second solution 22, preferably formaldehyde, and the separating means 31 constrained to it. FIG. 9b shows the opening of the first container 11 (in fact, the further lid 41 has been removed and is not in Figure) and the housing of a biological sample 10 inside the first container 11. FIG. 9c shows the tight closure of the first container 11 comprising the first solution 21, preferably the buffered solution, and the biological sample 10, thanks to the further lid 41. FIG. 9d shows another opening of the first container 11 (in fact, the further lid 41 has been removed and is not in Figure) and the housing of another biological sample 10 inside the first container 11. FIG. 9e shows the coupling of the first container 11 and second container 12, keeping the first solution 21, preferably buffered aqueous solution, and the second solution 22, preferably formaldehyde, separated. Finally, FIG. 9f shows the mixing of the first solution 21, preferably buffered solution, and second solution 22, preferably formaldehyde that has occurred, thus forming the fixative 23, preferably formalin, thanks to a manual action, for example further screwing of the second container 12 on the first container 11, thus allowing for example one or more impermeable membranes to be broken and/or lacerated (i.e., the separating means 31). The biological samples 10 are therefore "fixed" by the fixative 23.

Figure 10A:
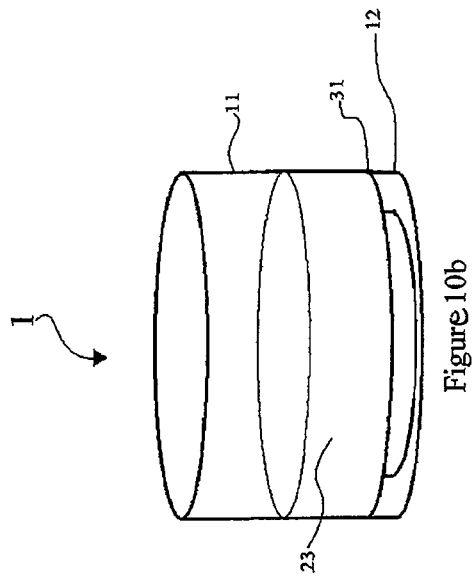
Figure 10B:
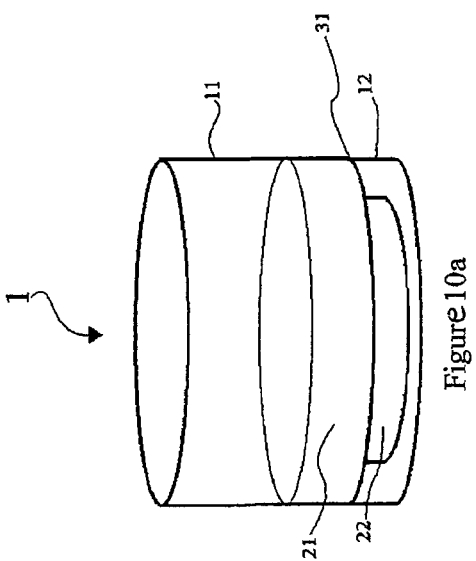

FIG. 10 is a schematic representation of the device 1 of the invention according to a further embodiment. In FIG. 10a it is possible to see the first container 11 comprising the first solution 21, preferably the buffered solution, the second container 12 comprising the second solution 22, preferably formaldehyde, and the separating means 31, all constrained to one another. Thanks to the pressure on the second container 12 towards the first container 11 (i.e., thanks to a manual action), the mixing of the first solution 21, preferably the buffered solution, with the second solution 22, preferably with formaldehyde, is occurring, and in FIG. 10b it is possible to see that the mixing of the first and second solutions has occurred thanks to the presence of the fixative 23, preferably formalin, in the first container 11. In fact, the pressure on the second container 12 allowed the rupture of the separating means 31, in this embodiment impermeable membranes, that kept the two solutions distinct and separate.

FIG. 11 is a schematic representation of the device 1 of the invention according to another embodiment. In FIG. 11a it is possible to see the first container 11 comprising the first solution 21, preferably the buffered solution, coupled to a further lid 51 adapted to open and tightly close the first container 11, and the second container 12 comprising the second solution 22, preferably formaldehyde. Said further lid 51 can be, for example, a lid known in the art with a tight closure, for example a threaded plug, that has a pierceable and self-sealing membrane, i.e. a membrane that can be pierced one or more times by a perforating means, such as a needle, and that can be re-closed once the perforating means, for example the needle, has been slipped off. Said second container 12, according to this embodiment, can be a syringe pre-filled with an exact predetermined amount of second solution, preferably formaldehyde (i.e., about 4% by weight with respect to the volume of formalin), or else a conventional syringe, in this case being used to withdraw the exact predetermined amount of said second solution 22, preferably formaldehyde (about 4% by weight with respect to the volume of formalin) from a container comprising the second solution 22, preferably formaldehyde (not shown in Figure). The latter can be a container especially used for the sampling by the syringe, and accordingly is configured so that to not expose the operator, who is filling the syringe, to the vapors and/or the contact with the second solution 22, for example with formaldehyde, or else it can be a conventional container of the second solution 22, and in such a case the filling operation of the syringe must be carried out under a chemical hood, for example in the analysis laboratory. In FIG. 11b it is possible to see the opening of the first container 11 and the housing of a biological sample 10 inside the first container 11. In FIG. 11c it is possible to see the tight closure of the first container 11 comprising the first solution 21, preferably the buffered solution, and the biological sample 10, thanks to the further lid 51. In FIG. 11d it is possible to see another opening of the first container 11 and the housing of another biological sample 10 inside the first container 11. In FIG. 11e it is possible to see the coupling of the first container 11 and second container 12, keeping the first solution 21, preferably buffered aqueous solution, and the second solution 22, preferably formaldehyde, separated. In this embodiment, the two solutions are kept separated thanks to the function of the syringe to retain the liquids, i.e. thanks to the pressure difference between the inside and the outside and/or to the needle capillarity. Finally, in FIG. 1 if it is possible to see that the occurred mixing of the first solution 21, preferably the buffered solution, with the second solution 22, preferably formaldehyde, thus forming the fixative 23, preferably formalin, thanks to the manual action executed on the plunger of the syringe.

In all of the Figures, the proportions of the dimensions of the first container 11 and the second container 12, as well as the proportions of buffered solution 21 and formaldehyde 22, are not the actual ones.

The invention claimed is:

1. Device for collecting, preserving and/or transporting isolated biological samples, comprising:
   a first container adapted to house said biological samples, which comprises a predetermined amount of a first solution; and
   a second container comprising a predetermined amount of a second solution,
   said first and second solutions forming "in situ" a fixative and said first and second containers being couplable to each other, said device further comprising separating means adapted to keep said first solution and said second solution distinct and separate, said first and second containers being configured so that to allow said first solution and said second solution to be mixed when said containers are coupled, thanks to a manual action on said containers and/or said separating means, thus obtaining said fixative "in situ", wherein said first container comprises of:
   a reservoir containing said predetermined amount of said first solution; and
   a female cap comprising puncturing means, said first container being freely opened and tightly closed thanks to the coupling between said female cap and said reservoir; and
   said second container comprises a predetermined amount of said second solution, and is a male cap comprising the separating means;
   said first container further comprising an impermeable and adhesive removable film adhering to said female cap and sized to tightly close said first container,
   said female cap adapted to be directly coupled to each of said reservoir and said male cap to enable tight closing of said device and allowing fluid connection between said reservoir and said male cap,
   wherein each of the female cap, the reservoir and the male cap include threaded portions such that said female cap includes a first threaded portion adapted to be directly screwed to a corresponding threaded portion of said reservoir, and a second threaded portion adapted to be directly screwed to a corresponding threaded portion said male cap,
   wherein said first solution is an aqueous solution buffered at pH values between 6.0 and 8.0, said second solution is formaldehyde and said fixative is formalin, and wherein said device further comprises a further lid adapted to open and tightly close the first container, said further lid allowing said first and said second container to be handled separately when said first and said second container are decoupled,
   wherein the female cap is a unitary piece.

2. The device according to claim 1, wherein said first solution is buffered at pH values between 6.7 and 7.4.

3. The device according to claim 1, wherein said predetermined amount of buffered aqueous solution is between 94% and 98% by weight with respect to the total volume of formalin, and said predetermined amount of formaldehyde is between 2% and 6% by weight with respect to the total volume of formalin.

4. The device according to claim 1, wherein said puncturing means are a cross punch.

5. The device according to claim 1, wherein said fluid connection is achieved by means of one or more holes that are on said female cap.

6. The device according to claim 5, wherein said one or more holes are circular sector openings.

7. A device Device-for collecting, preserving and/or transporting isolated biological samples, comprising:
   a first container adapted to house said biological samples, which comprises a predetermined amount of a first solution; and
   a second container comprising a predetermined amount of a second solution,
   said first and second solutions forming "in situ" a fixative and said first and second containers being couplable to each other, said device further comprising separating means adapted to keep said first solution and said second solution distinct and separate, said first and second containers being configured so that to allow said first solution and said second solution to be mixed when said containers are coupled, thanks to a manual action on said containers and/or said separating means, thus obtaining said fixative "in situ", wherein said first container comprises of:
   a reservoir containing said predetermined amount of said first solution; and
   a female cap comprising puncturing means, said first container being freely opened and tightly closed thanks to the coupling between said female cap and said reservoir; and
   said second container comprises a predetermined amount of said second solution, and is a male cap comprising the separating means;
   said first container further comprising an impermeable and adhesive removable film adhering to said female cap to tightly close said first container,
   said female cap adapted to be directly coupled to each of said reservoir and said male cap to enable tight closing of said device and allowing fluid connection between said reservoir and said male cap,
   wherein each of the female cap, the reservoir and the male cap include threaded portions such that said female cap includes a first threaded portion adapted to be directly screwed to a corresponding threaded portion of said reservoir, and a second threaded portion adapted to be directly screwed to a corresponding threaded portion said male cap,
   wherein said first solution is an aqueous solution buffered at pH values between 6.0 and 8.0, said second solution is formaldehyde and said fixative is formalin, and wherein said device further comprises a further lid adapted to open and tightly close the first container, said further lid allowing said first and said second container to be handled separately when said first and said second container are decoupled, wherein the female cap is a unitary piece and the first threaded portion and the second threaded portion of the female cap each face inwardly.

8. A device Device for collecting, preserving and/or transporting isolated biological samples, comprising:
   a first container adapted to house said biological samples, which comprises a predetermined amount of a first solution; and
   a second container comprising a predetermined amount of a second solution,
   said first and second solutions forming "in situ" a fixative and said first and second containers being couplable to each other, said device further comprising separating means adapted to keep said first solution and said second solution distinct and separate, said first and second containers being configured so that to allow said first solution and said second solution to be mixed when said containers are coupled, thanks to a manual action on said containers and/or said separating means, thus obtaining said fixative "in situ", wherein said first container comprises of:
   a reservoir containing said predetermined amount of said first solution; and
   a female cap comprising puncturing means, said first container being freely opened and tightly closed thanks to the coupling between said female cap and said reservoir; and
   said second container comprises a predetermined amount of said second solution, and is a male cap comprising the separating means;
   said first container further comprising an impermeable and adhesive removable film adhering to said female cap to tightly close said first container,
   said female cap adapted to be directly coupled to each of said reservoir and said male cap to enable tight closing of said device and allowing fluid connection between said reservoir and said male cap,
   wherein each of the female cap, the reservoir and the male cap include threaded portions such that said female cap includes a first threaded portion adapted to be directly screwed to a corresponding threaded portion of said reservoir, and a second threaded portion adapted to be directly screwed to a corresponding threaded portion said male cap,
   wherein said first solution is an aqueous solution buffered at pH values between 6.0 and 8.0, said second solution is formaldehyde and said fixative is formalin, and wherein said device further comprises a further lid adapted to open and tightly close the first container, said further lid allowing said first and said second container to be handled separately when said first and said second container are decoupled,
   wherein the female cap is a unitary piece, the first threaded portion peripherally surrounds the second threaded portion of the female cap and each of the first and second threaded portions faces inwardly.

* * * * *